United States Patent
MacAdam et al.

(10) Patent No.: US 6,968,227 B2
(45) Date of Patent: *Nov. 22, 2005

(54) METHODS FOR PROCESSING ELECTROCARDIAC SIGNALS HAVING SUPERIMPOSED COMPLEXES

(75) Inventors: David MacAdam, Millbury, MA (US); Paul J. Wang, Chestnut Hill, MA (US); Shawn Yang, Andover, MA (US); Dipen Shah, Geneva (CH)

(73) Assignee: C.R. Bard, Inc., Murray Hill, NJ (US)

( * ) Notice: Subject to any disclaimer, the term of this patent is extended or adjusted under 35 U.S.C. 154(b) by 405 days.

This patent is subject to a terminal disclaimer.

(21) Appl. No.: 10/005,470

(22) Filed: Nov. 7, 2001

(65) Prior Publication Data

US 2002/0091330 A1    Jul. 11, 2002

Related U.S. Application Data

(60) Provisional application No. 60/295,217, filed on Jun. 1, 2001, provisional application No. 60/247,269, filed on Nov. 10, 2000.

(51) Int. Cl.⁷ ................................................ A61B 5/04
(52) U.S. Cl. ......................................................... 600/515
(58) Field of Search ................................. 600/508–525

(56) References Cited

U.S. PATENT DOCUMENTS

| | | | |
|---|---|---|---|
| 4,721,114 A * | 1/1988 | DuFault et al. | 600/509 |
| 5,215,098 A * | 6/1993 | Steinhaus et al. | 600/515 |
| 5,311,873 A | 5/1994 | Savard et al. | |
| 5,609,157 A | 3/1997 | Panescu et al. | |
| 5,666,959 A * | 9/1997 | Deans et al. | 600/511 |
| 5,713,367 A | 2/1998 | Arnold et al. | |
| 5,772,604 A | 6/1998 | Langberg et al. | 600/518 |
| 5,827,195 A | 10/1998 | Lander | |
| 5,840,038 A * | 11/1998 | Xue et al. | 600/512 |
| 5,876,350 A * | 3/1999 | Lo et al. | 600/519 |
| 6,556,860 B1 * | 4/2003 | Groenewegen | 600/509 |
| 6,615,075 B2 * | 9/2003 | Mlynash et al. | 600/513 |

FOREIGN PATENT DOCUMENTS

| | | | |
|---|---|---|---|
| EP | 0 848 965 A2 | 6/1998 | |
| WO | 91/02484 | 3/1991 | ........... A61B 5/04 |
| WO | 01/67950 | 9/2001 | ........... A61B 5/04 |
| WO | WO-02/058550 A2 | 8/2002 | |
| WO | WO-03/022148 A1 | 3/2003 | |

OTHER PUBLICATIONS

John P. Marenco, et al., "Testing of a New T-Wave Subtraction Algorithm as an Aid to Localizing Ectopic Atrial Beats", A.N.E., Jan. 2003, vol. 8, No. 1, pp. 55-59.

Shelly A. Stevenson, et al., "Analysis of the Intraventricular Electrogram for Differentiation of Distinct Monomorphic Ventricular Arrhythmias", PACE—Pacing and Clinical Electrophysiology, Nov. 1997, vol. 20, No. 11, pp. 2730-2738.

PCT International Search Report dated Nov. 21, 2002 for counterpart International patent application PCT/US01/46348.

(Continued)

*Primary Examiner*—George Manuel
(74) *Attorney, Agent, or Firm*—Darby & Darby

(57) ABSTRACT

Computer implemented methods and associated systems are disclosed for processing electrical signals recorded from the heart and, more particularly, for objectively deriving subcomponents and comparing signals and their sub-components.

50 Claims, 7 Drawing Sheets

OTHER PUBLICATIONS

P. W. Hsia et al., "Computer Arrhythmia Analysis in an Exercise System," Proc. Ann. Conf. On Eng. In Medicine and Biology, Chicago, Illinois, Sep. 30-Oct. 2, 1985, pg. 65.

S. E. Greenhut et al., "Template Matching Techniques for Electrophysiologic Signals: A Practical, Real-Time System for Detection of Ventricular Tachycardia," Biomedical Sciences Instrumentation, 1992, pp. 37-42.

G. F. Mitchaud et al., "Correlation Waveform Analysis to Discriminate Monomorphic Ventricular Tachycardia from Sinus Rhythm Using Stored Electrograms from Implantable Defibrillators," Pace - Pacing and Clinical Electrophysiology, Futura Publishing Company, Inc., vol. 22, No. 8, Aug. 1999, pp. 1146-1151.

R. D. Throne et al., Use of Tachycardia Templates for Recognition of Recurrent Monomorphic Ventricular Tachycardia, Proc. Computers in Cardiology Meeting, Jerusalem, Sep. 19-22, 1989, Washington, IEEE Comp. Soc. Press, U.S., pp. 171-174.

Communication Relating to the Results of the Partial International Search for International Patent Application Serial No. PCT/US01/46348, Aug. 8, 2002, European Patent Office-International Searching Authority.

* cited by examiner

METHODS FOR PROCESSING ELECTROCARDIAC SIGNALS HAVING SUPERIMPOSED COMPLEXES

This patent application claims the benefit of priority under 35 U.S.C. § 119 of U.S. Provisional Application Ser. No. 60/247,269, filed Nov. 10, 2000, entitled "Method for Viewing and Comparing ECG Signals Having Superimposed Complexes," and U.S. Provisional Application Ser. No. 60/295,217, filed Jun. 1, 2001, entitled "An Algorithm to Measure T-wave Subtraction Quality," the entirety of both of these applications being hereby incorporated by reference.

FIELD OF THE INVENTION

This invention relates to a method for processing electrical signals obtained from the heart and, more particularly, to a method for processing electrocardiac signals having superimposed sub-component complexes to enable tracking of native, paced and derived beat signals.

BACKGROUND OF THE INVENTION

Certain cardiac arrhythmias are triggered or initiated from a site in the heart tissue other than the sinus node. These arrhythmias are generally classified as being "focal" in nature. Treatment of focal arrhythmias generally involves locating the arrhythmogenic site and ablating it. One method for regionally locating the focal site is the use of a diagnostic 12 Lead ECG. The 12 Lead can be used in conjunction with pacing via a roving intracardiac catheter to pace map the heart. The theoretical basis of this method assumes that the paced 12 lead ECG will appear identical to the non-paced ECG if the cycle length (i.e., paced heart rate) and pacing site matches the non-paced heart rate and focal site of origin.

One problem with this method (in current practice) is the subjectivity involved in visually comparing a non-paced 12 Lead ECG to a paced 12 Lead ECG.

A second problem is the time consuming nature of the procedure in which, typically, a spontaneous ectopic beat is recorded and printed on paper. A roving mapping catheter is positioned at a likely site of ectopy, pacing is initiated, a recording is made, a printout is generated and a visual comparison is made by aligning the printouts from the spontaneous and paced beats over one another. This process is repeated in an iterative manner until the physician determines that a good match between the spontaneous ectopic beat and the paced beat is found.

A third problem arises when multiple arrhythmogenic foci are present and each focus produces a variant on the 12 Lead ECG. Better discrimination between these foci would be advantageous during pace mapping as well as during other EP procedures. (Ref.—Throne R D, Jenkins J M, Winston S A, et al. "Use of tachycardia templates for recognition of recurrent monomorphic VT." Comp. Cardiology 1989:171–174.)

A fourth problem involves the superimposition of the P-wave and T-wave components of the ECG. The electrocardiogram typically includes an initial impulse, termed the P-wave, emanating from the atria, followed by what is termed the QRS complex, emanating from the ventricles, which is followed by a T-wave resulting from repolarization of the ventricles (FIG. 1). Thus, a heart beat begins with the P-wave and ends with the T-wave, and the next heart beat begins with another P-wave.

The P-wave can be a valuable tool used by clinicians to diagnose the condition of the heart. Thus, clinicians will often monitor an electrocardiogram (ECG) of the heart to aid in the diagnosis of atrial and ventricular arrhythmias. This can be done in various ways, such as by monitoring the 12 Lead (surface) ECG in conjunction with observing the bioelectric activity recorded on intracardiac electrodes carried by a transthoracic catheter.

In some focal arrhythmias the atrial heart tissue begins to beat very rapidly as the focal origin moves from the sinus node to an ectopic site. Sometimes this higher heart rate is sustained over three or more beats and is termed a tachycardia. Other times the higher rate is intermittent and may be as short as one heart beat. In either case, the first beat of the atrial arrhythmia is usually initiated by what is termed a Premature Atrial Contraction ("PAC") which can result in the P-wave of a successive heart beat overlapping with the T-wave of the preceding beat (FIG. 2). Not only is this a physiologically compromised state for the heart to be in, but the clinician can no longer use the P-wave to diagnose the heart because it is obscured by the T-wave.

Accordingly, it will be apparent that there continues to be a need for a method that allows a clinician to Pace Map more effectively and in addition monitor the P-wave of a patient's heart beat, even when the P-wave is overlapping with a preceding T-wave. The instant invention addresses these needs.

And while T-wave subtraction is a useful method in electrophysiology procedures to unmask the ECG P-wave morphology of a PAC by subtracting a QRS_T template from a PAC, ECG baseline drift caused by respiration or body movement may cause certain variations on the results of T-wave subtraction. Thus, a further need remains in the art to quantitatively measure the quality of T-wave subtraction results, among other reasons to monitor the respiration variations on T-wave subtraction. The instant invention addresses this need as well.

SUMMARY AND OBJECTS OF THE INVENTION

The present invention, in certain aspects, provides a medical practitioner with a computerized method for objectively and efficiently performing real time pace mapping and other cardiac analyses, through the processing of incoming electrical signals which represent heart activity to display a derived P-wave without any overlap with a preceding T-wave during a PAC, and to allow the practitioner to objectively compare derived P-waves to determine if they are emanating from the same focus. As a direct consequence of the cardiac signal processing of the present invention, otherwise masked signals and correlations are identified among heart beats and segments of heart beats through calculations on acquired signals and/or derivations of new signals. The practitioner can be guided through visual aids such as bar graphs and overlaid cardiac signals of the quality of signal matches. These signal matches can assist in diagnosing a patient and in the effectiveness of an ongoing treatment, for example, an ablation procedure.

Due to timing and amplitude relationships among beats of a heart, there is the possibility that individual waveforms can be obscured or hidden. If a singular, unadulterated sub-component waveform is identified, and if this sub-component has similar timing characteristics that allow it to be synchronized with the composite waveform, then a subtraction process can be performed in accordance with an aspect of the invention to thereby derive the other sub-component waveform(s). Sub-component waveforms, either derived, native state, or pace induced, can be quantitatively compared to one another using correlation analysis. This analysis may be done retrospectively or in real time.

More specifically, the present invention provides systems, programmed machines, and methods that permit superior signal processing over prior art electrophysiology signal processors and can achieve this using a standard 12 lead ECG.

In accordance with one aspect of the invention, a system for tracking ectopic beats comprises a signal sensing unit, a signal processor, and an output device. The signal sensing unit is configured to capture a first ECG signal. The signal processor is connected to receive the first ECG signal from the signal sensing unit and is configured to permit a user to mark a begin point and an end point of the first ECG signal for use in defining a waveform segment as a reference template, to acquire data from multiple leads, and to identify a best fit between the reference template and the acquired data using a correlation coefficient calculation. The output device presents the identified best fit.

In accordance with another aspect of the invention, a system for deriving a p-wave signal from a premature atrial contraction ("PAC") beat comprises a signal sensing unit, a signal processor, and an output device. The signal processor is connected so as to receive electrocardiac signals from the signal sensing unit and is configured to process the electrocardiac signals so as to derive the p-wave signal from the PAC beat. The output device presents the derived p-wave signal.

In a particular embodiment of the foregoing system, the processor is configured to execute the steps of: (a) selecting a QRS-T segment of a reference ECG signal; (b) permitting a user to mark a begin point and an end point of the selected ECG signal; (c) defining a reference template as being a waveform segment between the marked begin and end points of the selected ECG signal; (d) acquiring the PAC beat at the signal processing unit from multiple leads (preferably with no more than 12 leads); and (e) processing the PAC beat so as to derive the p-wave signal.

In accordance with still another aspect of the invention an electrophysiology computer system includes a processor that is configured to derive a p-wave signal hidden within a premature atrial contraction ("PAC") beat. The processor executes the steps of: (a) selecting a QRS-T segment of a reference ECG signal; (b) permitting a user to mark a begin point and an end point of the selected segment of the reference ECG signal; (c) defining a reference template as being a waveform segment between the marked begin and end points of the selected segment of the reference ECG signal; (d) acquiring the PAC beat at the signal processing unit from multiple ECG leads; and (e) processing the PAC beat so as to derive the p-wave signal.

In a particular embodiment of the foregoing system, the processor utilizes a correlation coefficient calculation to effect a subtraction of the reference template from a predetermined segment of the PAC beat. In more particular embodiments, the processor is configured to compare derived p-waves from multiple beats to one another, to indicate or infer a common focal origin among several derived p-waves, to predict the most likely site of the origin of a focus using a (preferably 12 lead) library of p-waves of known focal origin, to derive paced p-waves for comparison to spontaneous p-waves, to determine an integral value of the QRS area of a derived p-wave signal, to normalize any integral values over a length of the derived p-wave signal, to process the QRS segment of a beat separately to arrive at further determinations concerning the heart beat data, and to perform combinations of the foregoing.

In accordance with still another aspect of the invention an electrophysiology computer system includes a processor that is configured to execute steps substantially in the same manner as the processor that derives a p-wave from a PAC beat, but more generally is configured to derive a non-synchronous subcomponent from a first heartbeat signal having a composite waveform which includes a synchronous subcomponent overlapping the non-synchronous subcomponent. The processor executes the steps of selecting a synchronous subcomponent of a second heartbeat signal which corresponds to the synchronous subcomponent of the first heartbeat signal; permitting a user to mark a begin point and an end point of the selected synchronous subcomponent; defining a reference template as being a waveform segment between the marked begin and end points of the selected synchronous subcomponent; acquiring the composite waveform of the first heartbeat signal at the signal processing unit from multiple leads; and processing the composite waveform beat so as to derive the non-synchronous subcomponent.

In accordance with yet further aspects of the invention, a method for tracking ectopic beats through template matching is described which includes the steps of: (a) capturing a first ECG signal in a signal processing unit; (b) permitting a user to mark a begin point and an end point of the captured first ECG signal; (c) defining a reference template as being a waveform segment between the marked begin and end points of the first ECG signal; (d) acquiring data at the signal processing unit; and (e) using a correlation coefficient calculation on the acquired data to identify a best fit between the reference template and the acquired data.

In accordance with further aspects of the invention, a method for deriving a p-wave signal from a premature atrial contraction ("PAC") beat is described which can assist a person in diagnosing a heart. This method includes the steps of: (a) selecting a QRS-T segment of a reference ECG signal; (b) permitting a user to mark a begin point and an end point of the selected segment of the reference ECG signal; (c) defining a reference template as being a waveform segment between the marked begin and end points of the selected segment of the reference ECG signal; (d) acquiring the PAC beat at the signal processing unit from multiple leads; and (e) processing the PAC beat so as to derive the p-wave signal.

In a particular embodiment of the foregoing methods, the PAC beat is processed using a correlation coefficient calculation to effect a subtraction of the reference template from a predetermined segment of the PAC beat. Also, the foregoing methods can include the additional steps of: comparing derived p-waves from multiple beats to one another; indicating or inferring a common focal origin among several derived p-waves; predicting the most likely site of the origin of a focus using a (preferably 12 lead) library of p-waves of known focal origin; deriving paced p-waves for comparison to spontaneous p-waves; determining an integral value of the QRS area of a derived p-wave signal; normalizing any integral values over a length of the derived p-wave signal; processing QRS segment of a beat separately to arrive at further determinations concerning the heart beat data, and performing combinations of the foregoing steps.

Further methods according to still further aspects of the invention include the determination of integrals concerning a section of the QRS_T segment and the processing of those integrals. A QRS segment integral can be used as a measure of the QRS residue, which is an indicator of the alignment or synchronization quality between the template QRS and the PAC QRS Furthermore, baseline drift can be monitored as a change of the QRS absolute peak (integral) value percentage between the template and the PAC. These methods are implemented by suitably configured computer processors.

Yet a further method in accordance with another aspect of the invention proceeds in substantially the same manner as when deriving a p-wave from a PAC beat, but more generally includes the selecting the synchronous subcomponent of the heartbeat signal, permitting a user to mark a begin point and an end point of the selected synchronous subcomponent, defining a reference template as being a waveform segment between the marked begin and end points of the selected synchronous subcomponent, acquiring the composite waveform at the signal processing unit from multiple leads, and processing the composite waveform beat so as to derive the non-synchronous subcomponent.

In accordance with a further aspect of the present invention, a template optimization method is disclosed which dynamically employs different templates. QRS beats that precede or follow a PAC can be selected manually or by action of a programmed machine in selecting and setting a new template for use in subsequent calculations. The method is implemented by suitably configured computer processors.

Other aspects, features and advantages of the invention can be more clearly understood from the following detailed description of exemplary embodiments and accompanying Drawing Figures.

DESCRIPTION OF THE DRAWING FIGURES

DETAILED DESCRIPTION OF THE PREFERRED EMBODIMENTS

To promote an understanding of the methods that can be practiced in accordance with preferred embodiments of the present invention, several pertinent aspects are discussed below under respective headings.

Template Matching/Pace Mapping

Any recorded ECG waveform can be used as a reference to compare to another recorded ECG waveform or to a real time ECG waveform. The comparison is performed in a two step process in which first a reference template is selected by the user to describe the beginning and end of an ECG waveform segment to be used as a comparison template. Next the user selects the region of data to be used for comparison—either from pre-recorded data or from the real time data stream. A suitably configured computer processor can find the best match against the reference template over the region specified, or in the case of real time analysis, find the best match updated over a defined period of time, for example every second. The criteria for "best match" utilizes a correlation coefficient calculation across all twelve leads of the ECG and finds the best alignment. A visual display showing the aligned reference beat (template) overlaid on the beat undergoing analysis give the user feedback as to the closeness of the match. A correlation coefficient calculated for each ECG lead gives a quantitative indicator of the match. A composite average is also calculated and is displayed in a unique color enhanced bar graph indicator which is especially useful when real time template matching is being performed. The composite average can be updated as a moving average over a preselected number of beats.

Template matching may be used to compare two spontaneous beats or it can be used to pace map, i.e., to compare a paced beat to a spontaneous beat. A Region of Interest (ROI) indictor can be manipulated by the user to exclude certain portions of the waveform from analysis. This is useful during pace mapping where pacing artifacts on the surface leads can be excluded from the region of analysis. The ROI indicator can also be used to specify a preference for T-wave or P-wave matching as they are oftentimes morphologically very similar.

T-Wave Subtraction

In one embodiment of the present invention, a method is provided whereby an ECG having an overlapping P and T wave is processed to remove the T-wave and thereby display the P-wave without any overlap, so that a clinician may observe the P-wave when performing a diagnosis of the heart.

Figure 1:
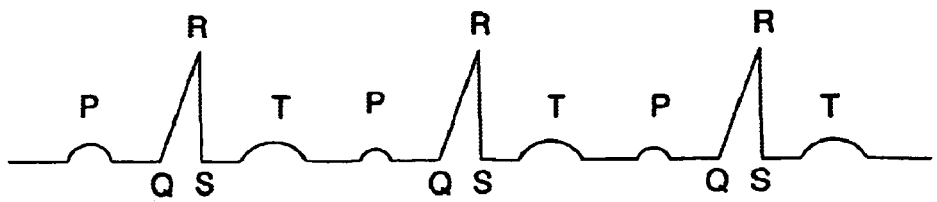
FIG. 1 is a schematic diagram of a normal heart beat.
Figure 2:
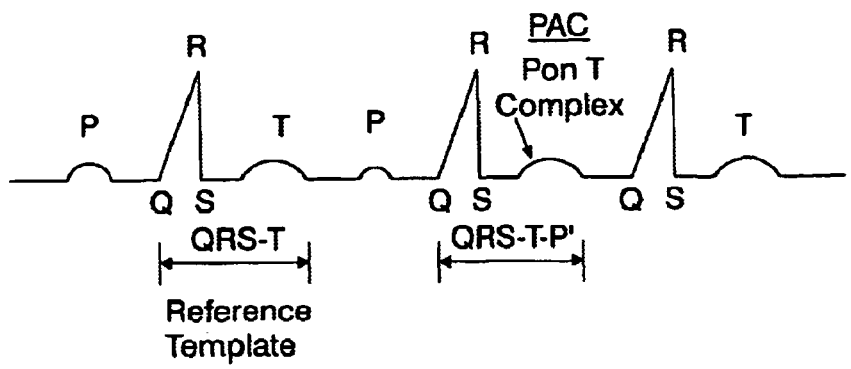
FIG. 2 is a schematic diagram of a pre-mature atrial contraction (PAC)

See FIG. 1 which describes a normal ECG over three beats in which distinctive P and T-waves can be identified. FIG. 2 shows a rhythm in which the P-wave from the third beat (P') arrives early and is obscured by the T-wave from the second beat. This results in what is termed a P on T complex, and is referred to as a QRS-T-P' in the figure.

In general, according to the method, the QRS-T segment of a beat that lacks a PAC is selected as a template. This template is subtracted from the QRS-T-P' signal in the PAC to be studied yielding the P-wave. The QRS-T signal used as the template may be from a single beat or it may be derived from an average of multiple beats. The QRS-T signal (or average) used as the template is selected so that the preceding QRS-QRS interval is equal (or nearly equal) to the QRS-QRS interval immediately preceding the QRS-T-P' signal to be studied. Preferably, the beat immediately preceding the PAC can be used for the selected QRS-T template as the cycle length and hemodynamic conditions of this beat are the closest to those of the succeeding beat that contains the PAC and P on T complex. (See FIGS. 2 and 3.)

The QRS complex is used as a means to synchronize and align the QRS-T template and the PAC beat for subtraction. The alignment is automated by the algorithm for the best match based on the composite correlation coefficient across the 12 Lead ECG. The practitioner has the option of shifting the template match left or right on a sample by sample basis with the resulting composite correlation coefficient updated at each new position. The practitioner also has the option of choosing the previous or following QRS-T segment as the reference template. The software will automatically locate the previous or following beat based on the current reference template and use the corresponding QRS-T segment of that beat as the new reference template in the calculation of derived P-waves.

Different display views showing the derived P-wave, alone, or overlaid with the original PAC beat or reference template are available as an aid to the practitioner.

P-waves that have been derived using the T-wave subtraction method can be signal processed further to remove unwanted artifacts caused by respiration or noise.

3. Template Matching of Derived P-Waves

Once one has a derived P-wave identified from the tachycardia or premature atrial beat (PAC), one can compare this derived P-wave with a previously captured reference template.

3a. More specifically, one or more spontaneous P-waves may be identified using the subtraction method described above and compared with one another using a correlation waveform analysis. This can be used to determine if the spontaneous P-waves have the same focal origin. This can be done in real time or in review from recorded data.

3b. In addition, one or more derived spontaneous P-waves may be identified and compared to a library of P-waves of known focal origin to predict the most likely site of origin.

3c. In addition, once a derived spontaneous P-wave is identified by the T-wave Subtraction method as described above then the practitioner can begin atrial pace mapping following the Template Matching/Pace Mapping method also described above. The roving pace mapping catheter is maneuvered within the atria (or adjacent vessels such as the pulmonary veins) until the derived paced P-wave is nearly identical to the derived spontaneous P-wave. This comparison of derived P-waves may be done on pre-recorded data or in real time.

More generally, two or more waveforms X,Y, . . . , may form a composite waveform that due to timing and amplitude relationships causes the individual waveforms to be obscured or hidden. The composite waveform includes includes a synchronous subcomponent overlapping a non-synchronous subcomponent. If a singular, unadulterated sub-component waveform (e.g. X or Y) can be identified, and if it has similar timing characteristics that allow it to be synchronized with the composite waveform (i.e., this identified subcomponent is the synchronous subcompent), then it can be subtracted from the composite waveform to derive the other subcomponent waveform(s) (i.e., the non-synchronous subcomponent(s)). Sub-component waveforms, either derived, native state, or pace induced, can be quantitatively compared to one another using correlation analysis. This analysis may be done retrospectively or in real time. One of skill in the art will appreciate that a number of algorithms can be used to compare waveform shape, including, but not limited to bin area methods and integrals; any of these methods can assist in the goals of aligning synchronous components of composite waveforms and/or comparing the derived results.

A method in accordance with this more general teaching proceeds generally as outlined above. Specifically, this method proceeds in substantially the same manner as when deriving a p-wave from a PAC beat, but more generally includes the selecting the synchronous subcomponent of the heartbeat signal, permitting a user to mark a begin point and an end point of the selected synchronous subcomponent, defining a reference template as being a waveform segment between the marked begin and end points of the selected synchronous subcomponent, acquiring the composite waveform at the signal processing unit from multiple leads, and processing the composite waveform beat so as to derive the non-synchronous subcomponent.

Figure 4:
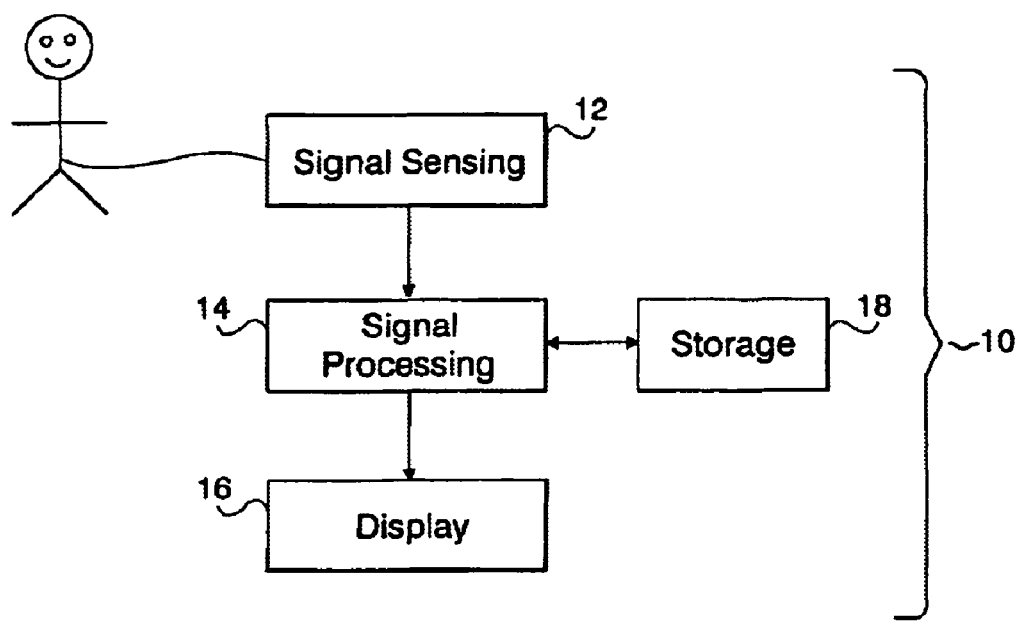
FIG. 4 is a block diagram of a system programmed to practice a method in accordance with a preferred embodiment of the present invention.

Referring now to the drawings, and particularly to FIG. 4, there is shown a system 10 for receiving and processing electrical signals according to one illustrative embodiment of the present invention. In one illustrative embodiment, the system 10 includes a signal sensing unit 12, which may take different forms, such as a standard 12 lead ECG, intracardiac lead, or combination thereof. The signal sensing unit is electrically connected to a signal processing device 14, which receives the sensed signals from the unit 12 and processes the signals, as is described in more detail below. The signal processing device ("signal processor" or "processor") 14 is preferably connected to a suitable display 16, which will present the processed signals to a clinician or other interested person. Information can be stored and recalled from a storage device 18. Preferably the signal processing device 14 and display 16 comprise the EP LabSystem (trademark) of C.R. Bard, Inc., Murray Hill, N.J., or the like. The EP LabSystem (trademark) supports a variety of data gathering and processing functions that are standard in electrophysiology procedures, and can have its hardware (namely, processor 14) configured to implement the subtraction and derivation methods set forth above, for example, through software (e.g., modules, procedures, functions, or objects) or firmware. The processor 14 communicates with a memory or storage 18 which configures the processor to implement the subtraction and derivation methods above (as well as the integral techniques described below).

In one illustrative embodiment, the special features of the system of the present invention are implemented, in part, by a processor using program information stored in a memory of the signal processing device 14. The processor 14 can access one or more files, as necessary, to implement the required functions, as described in greater detail in connection with FIG. 5 and FIG. 6.

Figure 5:
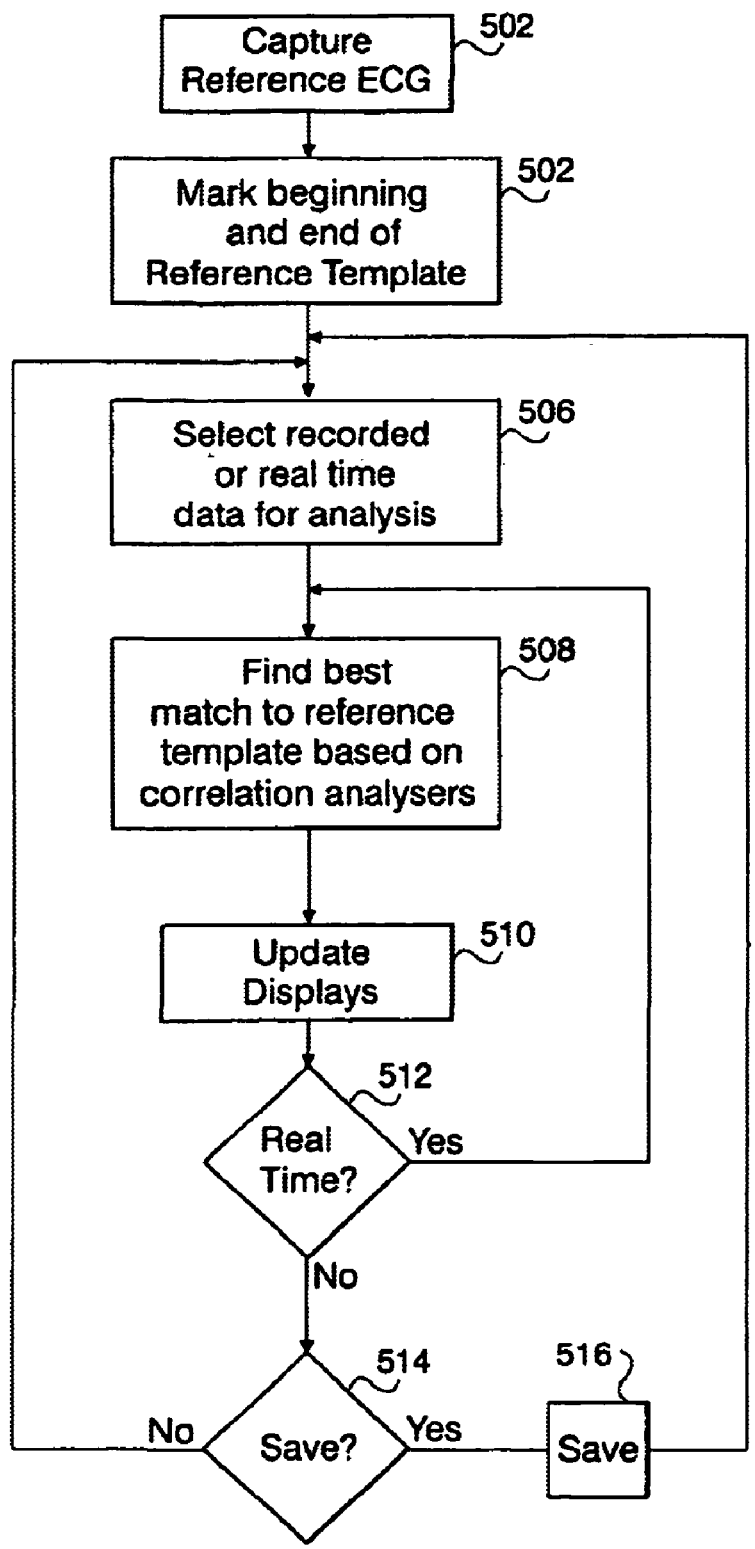
FIG. 5 is a flow diagram showing the process for template matching in accordance with the preferred embodiment.

Referring now to FIG. 5, the operation of the signal processing device 14 of the present invention is described in conjunction with the above structural description of the system 10. As illustrated in FIG. 5, the process begins when a clinician desires to create a reference template, and this occurs by capturing a reference ECG signal, as indicated at step 502. Preferably, the reference ECG signal is captured using a standard 12 lead device and/or one or more intracardiac leads. As explained above in connection with FIG. 2, the QRS-T signal components of a beat which does not exhibit P- on T-wave are selected as a template and it is this set of electrocardiac signal components that is captured at step 502. Such a beat can be captured in sinus rhythm or during a focal arrhythmia such as a tachycardia. Furthermore, it is contemplated that the reference template results from signals captured either at the surface, from intracardiac leads that can be placed in a variety of locations within the heart, or a combination of signals from surface and intracardiac leads. The QRS-T signal that is used as the template can be captured from a single heartbeat or may be a signal derived from an average of multiple heart beats.

At step 504, beginning and end points of the reference template are marked by the clinician using an interface to the signal processing unit 14. The marked points define the segment of the ECG waveform to be used as a comparison template.

At step 506, the clinician selects whether recorded or real-time data is to be used in the template matching analysis. (This step can be performed at any time prior to the waveform matching analysis at step 508, for example, prior to performing steps 502 and 504.) If recorded data is to be used in the template matching analysis, then a specified region of pre-recorded data is provided to the signal processing unit for comparison to the reference template. On the other hand, if real-time data is to be used in the template matching analysis, a stream of data from ECG leads is provided to the signal processing unit 14 over a defined period of time for comparison to the reference template.

At step 508, the signal processor 14 finds a "best match," in other words, a best alignment between the selected region or time period and the reference template.

At step 510, the display 16 is updated to indicate to the clinician (or other persons) the result of the template match. The results can be shown qualitatively as superimposed ECG waveform signals, namely, the reference beat (template) overlaid upon the beat under analysis to show the degree of alignment therebetween, or quantitatively as a correlation coefficient calculated for each ECG lead. Preferably, a composite average is also calculated and displayed. This is illustrated in the computer display shown in FIG. 8.

At step 512, a test is made to determine whether the user had selected real-time processing at step 506. If so, then the flow loops back to step 508 to again perform the template matching analysis and to update the display accordingly. Otherwise, if previously recorded segments are being analyzed, the user is given the option to save the analysis (as tested at step 514), and the correlation analysis is saved, as indicated at step 516. Real-time analyses can also be saved if desired.

Figure 6:
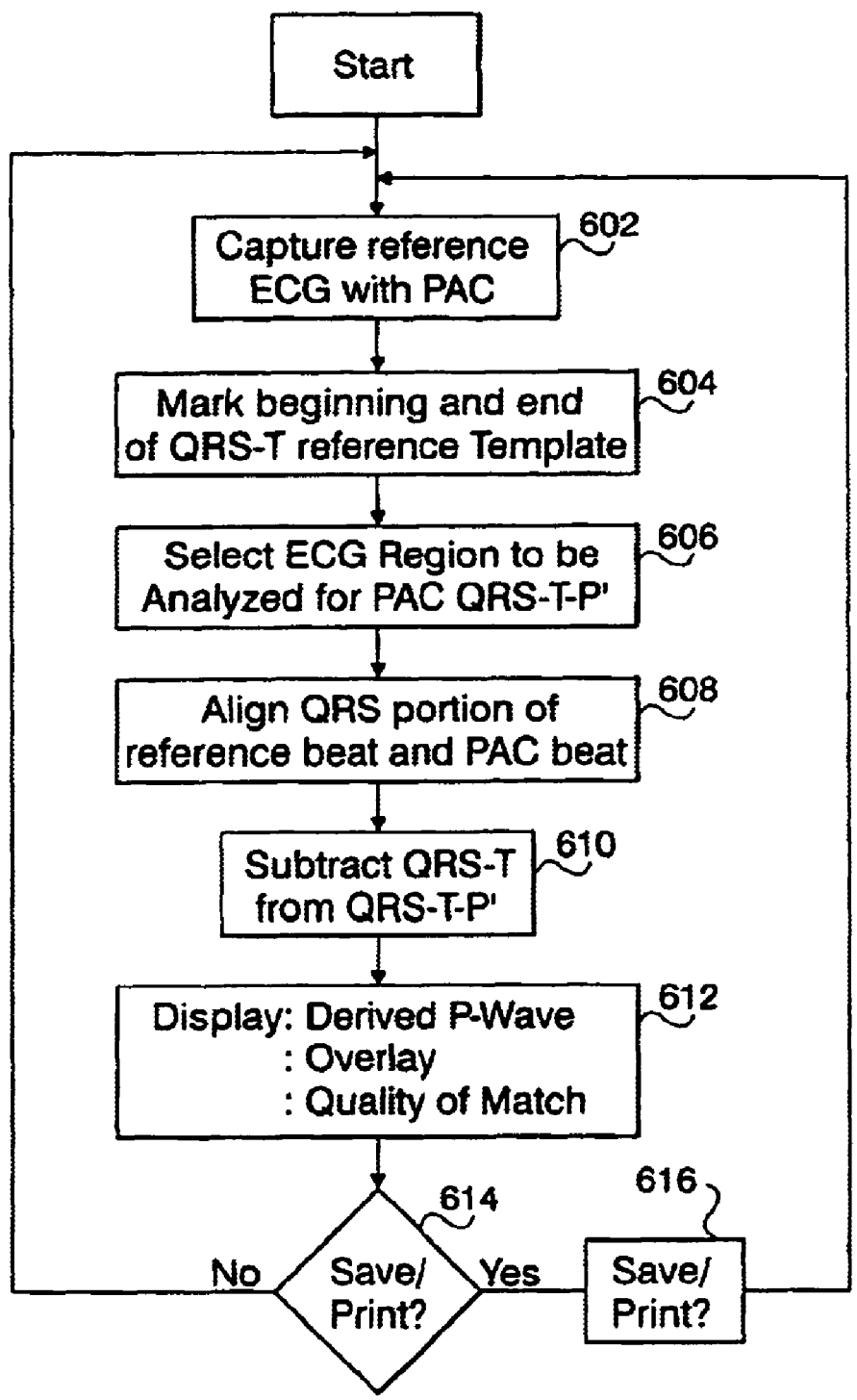
FIG. 6 is a flow diagram showing the process for T-wave Subtraction in accordance with the preferred embodiment.

Referring now to FIG. 6, the operation of the signal processing device 14 of the present invention is described in conjunction with the above structural description of the system 10. As illustrated in FIG. 6, the process begins at step 602 when a clinician captures a PAC and desires to subtract a QRS-T reference template from the PAC. The QRS-T reference template is marked by the clinician at step 604 (as described above) and a region encompassing the PAC is selected by the clinician at step 606 for analysis. The QRS portion of the reference template is aligned for best fit with the QRS complex immediately preceding the PAC at step 608. When the best fit is found, the processor 14 subtracts the QRS-T reference template from the QRS-T-P' segment of the PAC at step 610.

Figure 7:
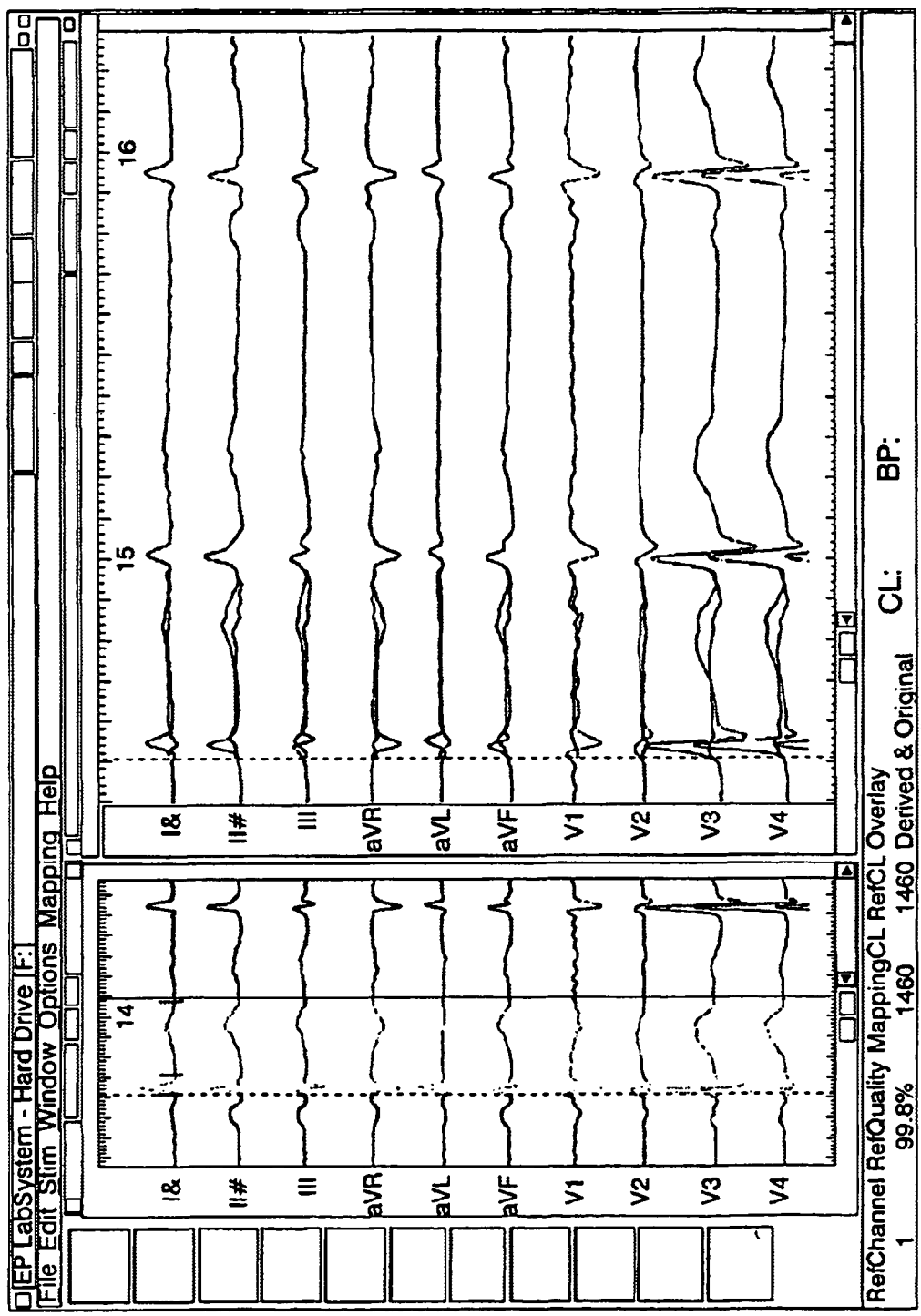
FIG. 7 is a representative computer display interface for T-wave subtraction that can be displayed to an operator.

The difference is the derived P-wave which is output to the display 16 at step 612. This is illustrated in the computer display shown in FIG. 7, in which the leftmost window displays the selected QRS-T reference template between two vertical lines (one dashed line prior to the 14 second mark at the top (highlighted by an arrow), and a second solid line just after the 14 second mark). The rightmost window shows the original PAC waveform with the derived P-wave overlaid on top of the portion of the ECG which occurs in the first 15 seconds. The overlaid and derived P-wave appears as a second graph superimposed over the ECG signals. Visual aids can be provided to automatically align and overlay waveforms for visual comparison on a computer display or a printout.

Figure 8:
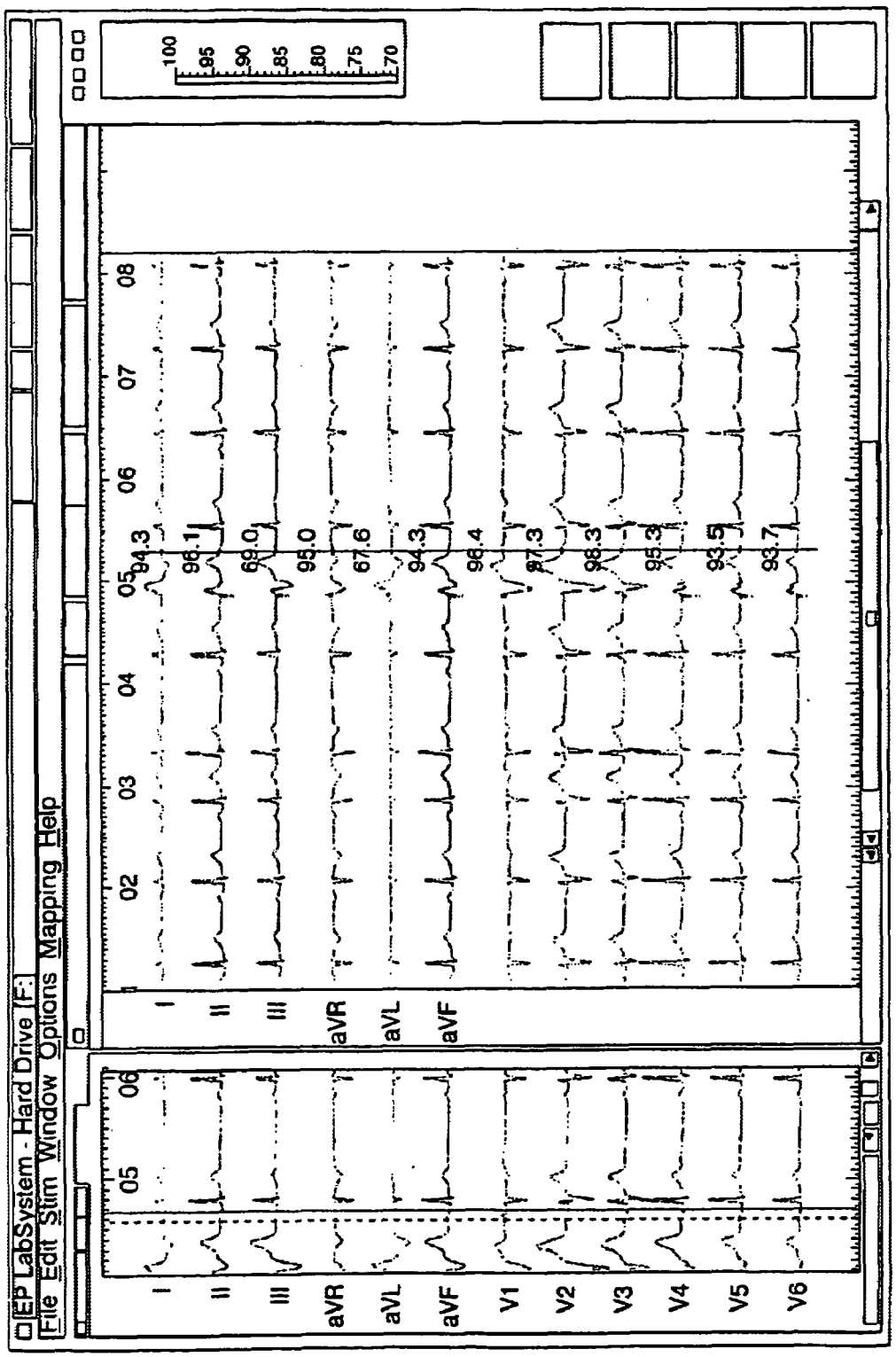
FIG. 8 is a representative computer display interface for template matching that can be displayed to an operator.

FIG. 8 illustrates an exemplary display for template matching (without subtraction) that can be displayed to an operator. The leftmost window displays markers which signify the presence and use of the reference template; the reference template beginning at the leftmost vertical line (highlighted by the arrow) and ends at the second vertical line. In this example, the reference template marks the start and finish of a P-wave; however, any waveform segment can be used if the region of interest has been marked for use as a template. The larger display window to the right shows the correlation value for each channel of the 12 Lead ECG as compared to the reference template. The bar graph at the far right is inactive in this example because the analysis region is taken from recorded data rather than real-time data gathered during a medical procedure.

The data can be saved, printed or both, if desired, in response to a user input to do so, as tested at step 614 and implemented at step 616.

From the foregoing, it will be apparent to those skilled in the art that the present invention provides a method for reliably and efficiently recovering a P-wave from a waveform that has overlapping P- and T-waves. Furthermore, the template matching capabilities of the invention provide the added benefit of quickly and objectively comparing ECG waveform components, in their native or derived state. It should also be understood that the correlation, subtraction and derivation methods described herein apply to data that can be acquired from conventional 12 lead surface ECG signals as well as intracardiac signals or combinations of both surface and intracardiac signals.

Two waveforms can have a high correlation to each other but still be poorly matched in absolute terms due to amplitude variation and drift caused by the effects of respiration. This can be a problem when two waveforms are aligned and then subtracted, one from the other. It is for this reason that immediately adjacent beats are usually desirable as the reference (QRS-T) and PAC (QRS-T-P'). This is not always possible and is not practical when performing real time pace mapping.

Figure 3:
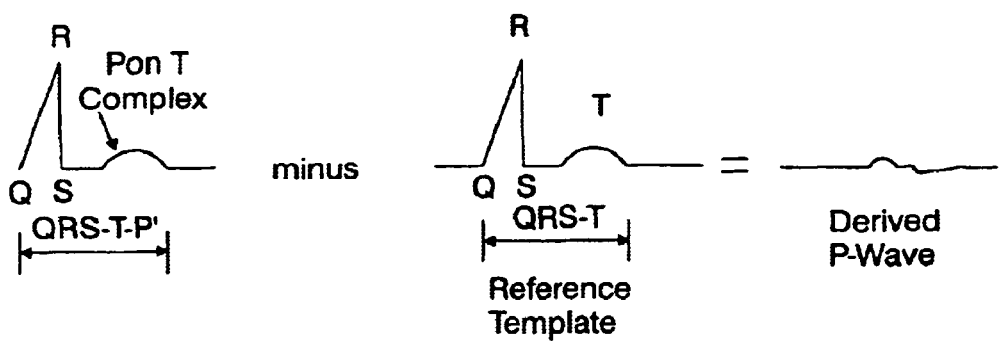
FIG. 3 is a schematic diagram of the T-Wave subtraction.
Figure 9:
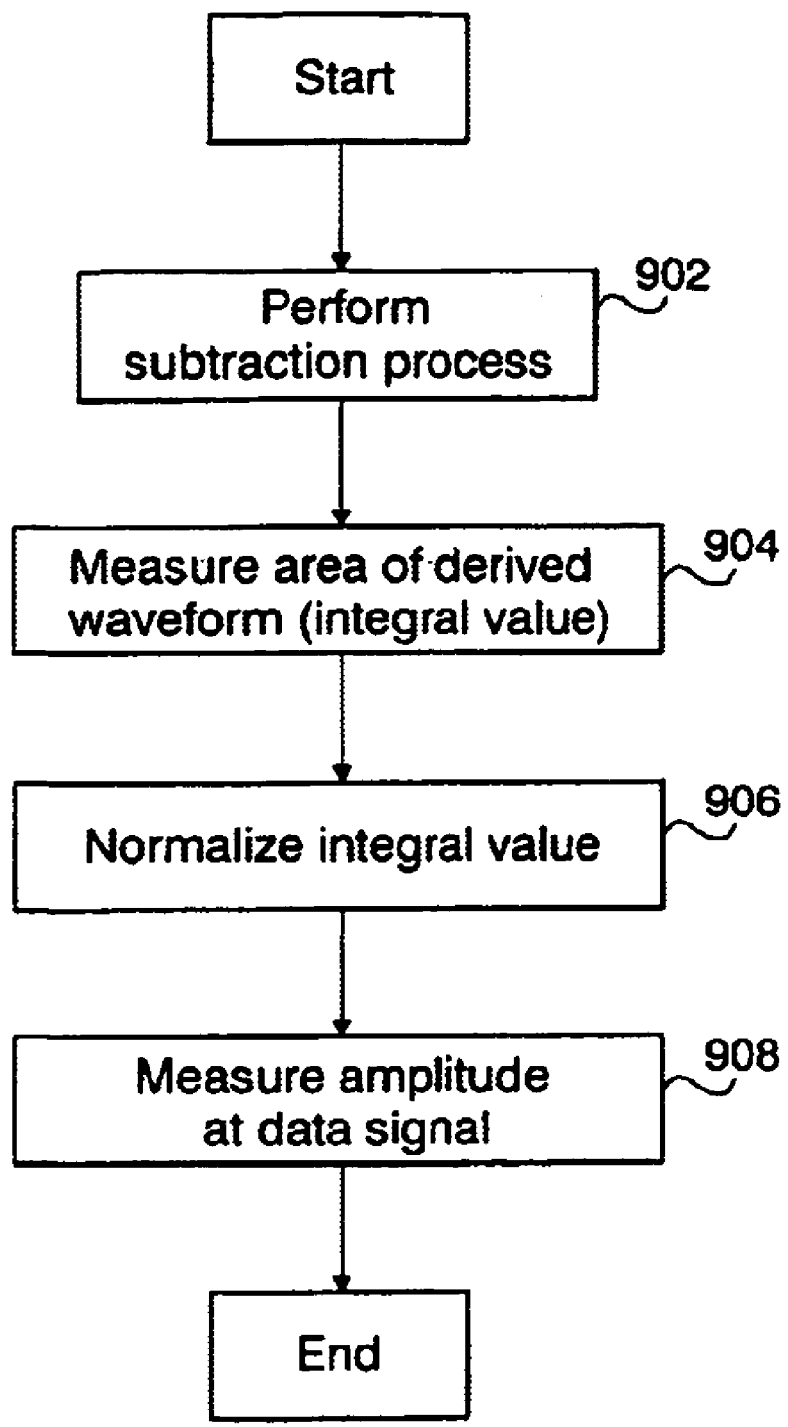
FIG. 9 illustrates a methodology for determining the integrals of a section of the QRS_T segment after the subtraction process.

A methodology for monitoring the quality of the T-Wave subtraction is now described with reference to FIG. 9. At step 902, a subtraction process (as illustrated in FIGS. 3 and 6 and described above) is performed to subtract a QRS-T template from a PAC (QRS-T-P') and thereby derive a waveform. The method of FIG. 9 proceeds by then providing integral calculations that enable a number of measurements of interest to practitioners, including, but not limited to: measures of QRS residue and the quality of the T-wave subtraction process; measures of the baseline drift, if any; and optimization of the selection of templates to be used in the subtraction process.

At step 904, the area of a derived waveform is measured. At step 906, the integral value is divided by the length of the derived waveform to normalize its value. In addition, at step 908, the amplitude of the normalized integral value is measured and displayed as a voltage at the ECG channel's input. This voltage value is termed the QRS residue. As described earlier, correlation analysis is used to align the QRS segment of a reference ECG template with the QRS segment of a PAC beat. Thus a further improvement may use the correlation coefficient in conjunction with the so-called QRS residue of the derived waveform to give an indication of the quality if the match between two beats chosen for subtraction. Together, they provide an indicator of the alignment or synchronization quality between the template QRS and the PAC QRS. For a perfect alignment and good subtraction results, the derived QRS segment should be flat indicating a high correlation to the template and the QRS residue should be very small indicating a small difference in absolute amplitudes (including drift).

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A method for tracking ectopic beats through template matching, comprising the steps of:
   (a) capturing a single ECG signal in a signal processing unit;
   (b) permitting a user to mark a begin point and an end point of the captured single ECG signal;
   (c) defining a reference template as being a waveform segment between the marked begin and end points of the single ECG signal;
   (d) acquiring data at the signal processing unit; and
   (e) using a correlation coefficient calculation on the acquired data to identify a best fit between the reference template and the acquired data;
   wherein an ectopic beat is tracked.

2. The method of claim 1, wherein the acquired data is acquired across multiple leads at a given point in time and is provided either from a data storage device or from a real-time data stream.

3. The method of claim 2, including the additional step of aligning on a display an image of the reference template with a beat within the acquired data across the multiple leads so as to display the extent of the identified best fit of the reference template with the acquired data from each of the multiple leads.

4. The method of claim 1, wherein the reference template is a segment of a spontaneous beat and wherein the acquired data is a paced beat.

5. The method of claim 1, wherein the reference template is a segment of a first spontaneous beat and wherein the acquired data is a second spontaneous beat which is different than the first spontaneous beat.

6. The method of claim 1, wherein the acquired data is from a real-time data stream, the method including the additional step of repeating the correlation coefficient calculation on the acquired data at a prescribed interval.

7. The method of claim 1 wherein the single ECG signal is captured by a lead.

8. The method of claim 7 wherein the lead is an intracardiac lead.

9. A method for tracking ectopic beats through template matching, comprising the steps of:
   (a) capturing a first ECG signal in a signal processing unit;
   (b) permitting a user to mark a begin point and an end point of the captured first ECG signal;
   (c) defining a reference template as being a waveform segment between the marked begin and end points of the first ECG signal;
   (d) acquiring data at the signal processing unit; and
   (e) using a correlation coefficient calculation on the acquired data to identify a best fit between the reference template and the acquired data; and
   (f) outputting a quantitative indicator of the correlation coefficient calculation;
   wherein an ectopic beat is tracked.

10. The method of claim 4, wherein the data is acquired from multiple leads and wherein the quantitative indicator is a composite average of coefficients calculated from the multiple leads.

11. The method of claim 10, wherein the quantitative indicator is displayed as a graph showing percentage of fit.

12. A method for deriving a p-wave signal from a premature atrial contraction ("PAC") beat to assist a person in diagnosing a heart, comprising the steps of:
   (a) selecting a QRS-T segment of a reference single ECG signal;
   (b) permitting a user to mark a begin point and an end point of the selected segment of the reference single ECG signal;
   (c) defining a reference template as being a waveform segment between the marked begin and end points of the selected segment of the reference single ECG signal;
   (d) acquiring the PAC beat at the signal processing unit from multiple leads; and
   (e) processing the PAC beat so as to derive the p-wave signal.

13. The method of claim 12, wherein the processing step comprises subtracting the reference template from a predetermined segment of the PAC beat.

14. The method of claim 12, wherein the reference ECG signal is a beat that immediately precedes the PAC beat.

15. The method of claim 12, including the additional step of synchronizing the reference template and the PAC beat by aligning respective waveform segments thereof.

16. The method of claim 15, wherein the alignment is by using a correlation coefficient calculation on the acquired data to identify a best fit between the respective waveform segments.

17. The method of claim 16, including the additional step of permitting the person to shift the alignment thereby causing a change in the correlation coefficient calculation.

18. The method of claim 16, including the additional step of permitting the person to shift the reference template to a waveform segment between corresponding begin and end points of a different beat thereby causing a change in the correlation coefficient calculation.

19. The method of claim 15, wherein the respective waveform segments are the QRS complexes of the reference template and the PAC beat.

20. The method of claim 19, wherein the alignment is by using a correlation coefficient calculation on the PAC beat to identify a best fit between the QRS complexes of the reference template and the PAC beat.

21. The method of claim 12, including the additional steps of:
   repeating the acquiring and processing steps so as to derive p-waves from at least two different PAC beats, and
   comparing the derived p-waves to one another.

22. The method of claim 21, wherein the comparing step comprises performing a cross correlation waveform analysis.

23. The method of claim 21, including the additional step of selectively indicating on an output device a quality of a match as a function of the comparing step to thereby provide an indicator as to whether the derived p-waves have the same focal origin.

24. The method of claim 12, including the additional steps of comparing the derived p-wave to a library of p-waves of known focal origin, and predicting the most likely site of the origin as a function of the comparison.

25. The method of claim 12, wherein the derived p-wave is a derived, spontaneous p-wave, the method including the additional steps of maneuvering a pace mapping catheter within or adjacent the atria while pacing the heart while repeating the acquiring and processing steps so as to derive a paced p-wave, and comparing the derived, paced p-wave to the derived, spontaneous p-wave.

26. The method of claim 25 wherein the derived, spontaneous p-wave defines a template and the comparing step comprises using a correlation coefficient to identify a best fit between the derived, spontaneous p-wave template and the derived, paced p-wave.

27. The method of claim 12, including the additional step of determining an integral value of the area of the derived p-wave signal.

28. The method of claim 27, including the additional step of normalizing the integral value over a length of the derived p-wave signal.

29. The method of claim 28, wherein the marked beginning and end points define a QRS segment of the reference ECG signal, the method including the additional step of measuring the QRS residue of the derived p-wave signal to provide an indicator of the alignment quality between the QRS segment of the PAC beat and a QRS segment of the reference template.

30. The method of claim 29, wherein the processing step comprises subtracting the reference template from the QRS segment of the PAC beat, and wherein the QRS residue is an integral value computed after the processing step.

31. The method as in claim 12, wherein the acquiring and processing steps are repeated, the method including the additional steps of:
calculating, for each iteration of the acquiring and processing steps, the integral value of the QRS segment of the reference template and the integral value of the PAC beat,
determining any change in absolute peak value percentage of the integral values between the reference template and the PAC beat,
whereby any baseline drift is identified.

32. The method of claim 12 wherein the single ECG signal is captured by a lead.

33. The method of claim 32 wherein the lead is an intracardiac lead.

34. A method for deriving a non-synchronous subcomponent from a first heartbeat signal having a composite waveform which includes a synchronous subcomponent overlapping the non-synchronous subcomponent in order to assist a person in diagnosing a heart, comprising the steps of:
(a) selecting a synchronous subcomponent of a second, single heartbeat signal which corresponds to the synchronous subcomponent of the first heartbeat signal;
(b) permitting a user to mark a begin point and an end point of the selected synchronous subcomponent of the second, single heartbeat signal;
(c) defining a reference template as being a waveform segment between the marked begin and end points of the selected synchronous subcomponent of the second, single heartbeat signal;
(d) acquiring the composite waveform of the first heartbeat signal at the signal processing unit from multiple leads; and
(e) processing the composite waveform beat so as to derive the non-synchronous subcomponent of the first heartbeat signal.

35. The method of claim 34, wherein the processing step comprises subtracting the reference template from a predetermined segment of the composite waveform.

36. The method of claim 34, wherein the selected synchronous subcomponent of the second, single heartbeat signal is from a beat that immediately precedes the composite waveform.

37. The method of claim 34, including the additional step of synchronizing the reference template and the composite waveform by aligning respective synchronous waveform segments thereof.

38. The method of claim 37, wherein the alignment is by using a correlation coefficient calculation on the acquired data to identify a best fit between the respective synchronous waveform segments.

39. The method of claim 38, including the additional step of permitting the person to shift the alignment thereby causing a change in the correlation coefficient calculation.

40. The method of claim 38, including the additional step of permitting the person to shift the reference template to a waveform segment between corresponding begin and end points of a different heartbeat thereby causing a change in the correlation coefficient calculation.

41. The method of claim 37, wherein the respective waveform segments are the synchronous subcomponents of the reference template and the composite waveform.

42. The method of claim 41, wherein the alignment is by using a correlation coefficient calculation on the composite waveform to identify a best fit between the synchronous subcomponents of the reference template and the composite waveform.

43. The method of claim 34, including the additional steps of:
repeating the acquiring and processing steps so as to derive non-synchronous subcomponents from at least two different composite waveforms, and
comparing the derived non-synchronous subcomponents to one another.

44. The method of claim 43, wherein the comparing step comprises performing a cross correlation waveform analysis.

45. The method of claim 43, including the additional step of selectively indicating on an output device a quality of a match as a function of the comparing step to thereby provide an indicator as to whether the derived non-synchronous subcomponents have the same focal origin.

46. The method of claim 34, including the additional step of determining an integral value of the area of the derived non-synchronous subcomponent.

47. The method of claim 46, including the additional step of normalizing the integral value over a length of the derived non-synchronous subcomponent.

48. The method of claim 34, including the additional steps of
comparing the derived non-synchronous subcomponent to a library of non-synchronous subcomponents of known focal origin, the derived non-synchronous subcomponent being a spontaneous non-synchronous subcomponent;
predicting the most likely site of the origin as a function of the comparison;
maneuvering a pace mapping catheter within or adjacent the heart while pacing the heart in real-time;
repeating the acquiring and processing steps so as to derive a paced non-synchronous subcomponent until such time that the derived, paced and spontaneous subcomponents correlate with one another within a prescribed criterion.

49. A method for deriving a non-synchronous subcomponent from a first heartbeat signal having a composite waveform which includes a synchronous subcomponent overlapping the non-synchronous subcomponent in order to assist a person in diagnosing a heart, comprising the steps of:
(a) selecting a synchronous subcomponent of a second heartbeat signal which corresponds to the synchronous subcomponent of the first heartbeat signal;

(b) permitting a user to mark a begin point and an end point of the selected synchronous subcomponent of the second, single heartbeat signal;

(c) defining a reference template as being a waveform segment between the marked begin and end points of the selected synchronous subcomponent of the second, single heartbeat signal;

(d) acquiring the composite waveform of the first heartbeat signal at the signal processing unit from multiple leads;

(e) processing the composite waveform beat so as to derive the non-synchronous subcomponent of the first heartbeat signal;

(f) comparing the derived non-synchronous subcomponent to a library of non-synchronous subcomponents of known focal origin; and (g) predicting the most likely site of the origin as a function of the comparison.

50. A method for deriving a non-synchronous subcomponent from a first heartbeat signal having a composite waveform which includes a synchronous subcomponent overlapping the non-synchronous subcomponent in order to assist a person in diagnosing a heart, comprising the steps of:

(a) selecting a synchronous subcomponent of a second, single heartbeat signal which corresponds to the synchronous subcomponent of the first heartbeat signal;

(b) permitting a user to mark a begin point and an end point of the selected synchronous subcomponent of the second, single heartbeat signal;

(c) defining a reference template as being a waveform segment between the marked begin and end points of the selected synchronous subcomponent of the second, single heartbeat signal;

(d) acquiring the composite waveform of the first heartbeat signal at the signal processing unit from multiple leads; and (e) processing the composite waveform beat so as to derive the non-synchronous subcomponent of the first heartbeat signal wherein the derived non-synchronous subcomponent is a derived, spontaneous non-synchronous subcomponent, the method including the additional steps of maneuvering a pace mapping catheter within or adjacent the atria while pacing the heart, and repeating the acquiring and processing steps so as to derive a paced non-synchronous subcomponent until such time that the derived paced and spontaneous subcomponents correlate with one another within a prescribed criterion.

* * * * *